United States Patent [19]
Hawley

[11] Patent Number: 5,095,888
[45] Date of Patent: Mar. 17, 1992

[54] INTUBATING STYLET FOR A LARYNGOSCOPE

[75] Inventor: Peter N. Hawley, Huntington, Conn.

[73] Assignee: Circon Corporation, Santa Barbara, Calif.

[21] Appl. No.: 549,354

[22] Filed: Jul. 9, 1990

[51] Int. Cl.⁵ .............................................. A61B 1/26
[52] U.S. Cl. .................................................. 128/10
[58] Field of Search ...................... 128/10, 11, 4, 6; 604/164, 165, 166

[56] References Cited

U.S. PATENT DOCUMENTS

| | | | |
|---|---|---|---|
| 3,598,113 | 8/1971 | Moore et al. | 128/11 |
| 3,643,654 | 2/1972 | Felbarg | 128/11 |
| 3,677,262 | 7/1972 | Zukowski | 128/6 |
| 3,760,797 | 9/1973 | Stauffer | 128/6 |
| 3,766,909 | 10/1973 | Ozbey | 128/11 |
| 3,771,514 | 11/1973 | Huffman et al. | 128/11 |
| 3,776,222 | 12/1973 | Smiddy | 128/6 |
| 3,913,568 | 10/1975 | Carpenter | 128/11 |
| 4,086,919 | 5/1978 | Bullard | 128/11 |
| 4,337,761 | 7/1982 | Upshur | 128/11 |
| 4,742,819 | 5/1988 | George | 128/6 |
| 4,773,394 | 9/1988 | Reichstein | 128/4 |
| 4,800,870 | 1/1989 | Reid, Jr. | 128/6 |
| 4,905,669 | 3/1990 | Bullard et al. | 128/11 |
| 4,947,829 | 8/1990 | Bullard | 128/11 |

Primary Examiner—William H. Grieb
Attorney, Agent, or Firm—Daniel J. Meaney, Jr.

[57] ABSTRACT

An intubating stylet adapted to be operatively connected to a laryngoscope having a shaped frame with a relatively rigid blade for positioning a workpiece, such as an endotracheal intubation tube, in the larynx and upper trachea region of a patient as shown. The intubating stylet comprises a relatively rigid preformed member having a central portion, a proximal portion and a distal portion. The elongated member is contoured from the central section to the distal section to substantially follow the shape of the shaped frame and rigid blade. The distal portion terminates in a distal tip which, in the preferred embodiment, is adapted to removable support the distal end of an endotracheal intubation tube. The elongated member is contoured from the central section to the proximal section to substantially follow the shape of the laryngoscope which extends in a direction opposite to the relatively rigid blade. The proximal portion terminates in a connecting member for operatively coupling the intubating stylet to the laryngoscope enabling the stylet to be moveable therewith.

A combination of an intubating stylet and endotracheal intubation tube forming a subassembly is also shown. A method for forming a subassembly of an intubating stylet and an endotracheal intubation tube which is to be adapted to be mounted onto the laryngoscope is also shown. A method of intubating a patient using the laryngoscope with the subassembly operatively attached thereto is also shown.

20 Claims, 5 Drawing Sheets

INTUBATING STYLET FOR A LARYNGOSCOPE

BACKGROUND OF THE INVENTION

1. Field of the Invention

The present invention relates to a rigid laryngoscope which includes an intubating stylet for supporting and inserting an endotracheal intubation tube into the laryngeal area of the human body and more particularly relates to a laryngoscope having a shaped frame with a relatively rigid blade and an intubating stylet operatively coupled thereto for positioning a workpiece, such as an endotracheal intubation tube, in the larynx and upper trachea region of a patient.

2. Description of the Prior Art

In the medical field and during performance of a surgical procedure in the human body, it is usually necessary to provide a positive air passage way for the administration of anesthesia and/or for mechanical inflation of the lungs of a patient. Typically, an endotracheal intubation tube is utilized as the means for providing the positive air passageway through the larynx and into the trachea region or tracheal area of a patient. However, in order to pass the endotracheal intubation tube through the larynx, it is necessary to displace the epiglottis which normally overlies the glottic opening into the larynx. The epiglottis functions to prevent the passage of foreign objects, such as, for example food, into the trachea. In performing an endotracheal intubation procedure on a patient, an initial step of the procedure is to displace the epiglottis from the glottal opening to permit the endotracheal intubation tube to pass through the larynx or vocal cords and be inserted into the trachea.

It is known in the medical field to utilize a laryngoscope to facilitate endotracheal intubation of a patient prior to surgery wherein an endotracheal intubation tube is inserted into the trachea to provide a positive air passageway which is used for the above described purposes.

Laryngoscopes are well known in the art. Laryngoscopes known in the art include structures comprising a rigid blade which can either be of a straight construction or a slightly curved construction. Examples of the known laryngoscopes are disclosed in U.S. Pat. Nos. 4,086,919; 3,598,113; 3,643,654; 3,766,909 and 3,771,514.

In addition, laryngoscopes are provided with a light guide to illuminate a working site or working area within the human body for visualization by the user and a fiber optic image bundle for transmitting an image from the working site through the laryngoscope to the proximal portion of the laryngoscope where the image can be viewed directly by the anesthetist or, as an alternative, the optical image is utilized as an input optical image to a video camera to produce a video image thereof. Typical of such laryngoscopes which include illumination means and optical image transporting means are U.S. Pat. Nos. 3,776,222; 3,913,568; 3,677,262 and 4,086,919.

It is also known in the art to have a laryngoscope include a working channel. One such laryngoscope is disclosed in U.S. Pat. No. 4,905,669. U.S. Pat. No. 4,905,669 discloses an intubation mechanism having a placement device which includes an elongated shaft which can be inserted into and moved within the working channel of the laryngoscope. During use, a laryngoscope having the intubating mechanism operatively mounted thereto is inserted into the mouth or oral cavity of a patient with the patient in the supine position. The laryngoscope performs the tasks of positioning the blade in the mouth of the patient displacing the tongue and exposing the glottis, all of which is accomplished by visual confirmation through a fiber optic image bundle. The intubation mechanism placement device includes a grasping means which is located at the distal region of the elongated shaft. The grasping means is adapted to grasp, hold and release at least a portion of a workpiece, such as the Murphy Eye of an endotracheal intubation tube. The intubation mechanism enables the workpiece to be grasped and moved with the laryngoscope and when the workpiece is in the desired position it can then be released from the grasping means and be advanced into the desired location.

In the alternative, a malleable stylet may be used in lieu of the intubating mechanism. In use, the malleable stylet is passed through an endotracheal intubation tube to form a separate subassembly which is then inserted adjacent the laryngoscope, past the larynx or vocal cords and into the trachea of the patient.

By use of the laryngoscope having the intubation mechanism or by use of a malleable stylet, an endotracheal intubation tube is transported past the displaced epiglottis through the glottic opening into the trachea of a patient.

SUMMARY OF THE INVENTION

The laryngoscope having working channel described in U.S. Pat. No. 4,905,669 requires the anesthetist to have a high level of dexterity and good hand-to-eye coordination in order to simultaneously hold the laryngoscope in the right hand and to manipulate the intubation mechanism with the right thumb while using the left hand to manipulate the endotracheal intubation tube and cause the jaws of the intubation mechanism to release the endotracheal intubation tube, all concurrently.

Another problem associated with the use of a laryngoscope as described in U.S. Pat. No. 4,905,669 in combination with a malleable stylet in lieu of the intubation mechanism is that the anesthetist must first manually shape or form the malleable stylet to the desired shape, insert the malleable stylet into an endotracheal intubation tube, then slide the subassembly adjacent the laryngoscope into the laryngeal area and then to pass the same through glottis opening into the larynx and ultimately into proper position within the trachea of the patient.

During an anesthesia procedure, considerable skill and time is required to form the malleable stylet into the proper position, to load the endotracheal intubation tube thereon to form the subassembly and then to successfully pass the subassembly into the mouth of the patient through the larynx or vocal cords into the trachea, under visual confirmation, in order to complete the procedure.

Another disadvantage of utilizing a malleable stylet in combination with the endotracheal intubation tube is that if a bend, too sharp or too slight, is formed in the assembly, this may result in a failed intubation. In such event, reshaping of the malleable stylet and the endotracheal intubation tube loaded thereon may be required, all of which complicates the intubation procedure.

Another disadvantage of the prior art intubation devices which utilize a malleable stylet is that the malleable stylet loses the shape during the introduction into the oropharynx. In certain procedures, it will be necessary for the anesthetist to remove the malleable stylet and endotracheal intubation tube loaded thereon and to reshape the stylet before reinserting the same into the patient. In an emergency situation, this is undesirable.

Another disadvantage of the prior art device is that when a malleable stylet has been used several times, it loses the ability to maintain its shape. Thus, an anesthetist, in order to avoid this problem, may use a new stylet with each intubation since any inconsistencies arising from prior use may inhibit a smooth introduction of the stylet having the endotracheal intubation tube loaded thereon.

Another disadvantage of the prior art device is that the malleable stylet must be introduced independently of the laryngoscope.

Another disadvantage of the prior art device is that difficulties exist in developing the hand-eye coordination required to direct the stylet into the endotracheal intubation tube by viewing the same through a remote eyepiece or viewing a video image thereof. Typically, an anesthetist is required to perform many procedures before developing the hand-eye coordination and required to perform a speedy and accurate endotracheal intubation procedure.

Of course, all the above disadvantages have the potential of being harmful to the anatomy of a patient during a rough introduction thereof.

The present invention discloses a new, novel and unique device which represents a substantial advancement in the state of the art. In the preferred embodiment of the present invention, a laryngoscope having a shaped frame with a relatively rigid blade and an intubating stylet operatively coupled thereto is used for positioning a workpiece in the larynx and upper trachea region of a patient. In the preferred embodiment, the workpiece is a endotracheal intubation tube having a Murphy Eye formed therein and having a typical inflatable sealing means (commonly known as cuff) and means for inflating the sealing means to form a seal when the endotracheal intubation tube is in place in the trachea.

In the preferred embodiment, the intubating stylet comprises a relatively rigid preformed elongated member having a distal section, a proximal section and a central section therebetween. The central section is a preformed shape. The distal section thereof terminates in a distal tip for removable supporting a workpiece. The proximal portion of the elongated member terminates in a connecting means for operatively coupling the intubating stylet to the laryngoscope so that it is removable therewith.

Also, a subassembly comprising an endotracheal intubation tube mounted upon the intubating stylet is another teaching of the present invention.

The present invention overcomes several other disadvantages associated with the prior art laryngoscope intubation mechanism or malleable stylet for use with a laryngoscope.

One advantage of the present invention is that the intubating stylet having an endotracheal intubation tube operatively attached thereto is placed behind the anatomically shaped blade of a laryngoscope. The laryngoscope having the intubating stylet and endotracheal intubation tube operatively attached thereto is rotated from the horizontal position to the vertical position by the user and the laryngoscope in combination with the intubating stylet and endotracheal intubation tube simultaneously slide around the tongue inserted into the oropharynx in the vicinity of the posterior pharynx. When the laryngoscope is in position, the endotracheal intubation tube is then advanced off of the intubating stylet and transported between the vocal cords and into the trachea. The laryngoscope and the intubating stylet are then removed simultaneously from the oropharynx and the intubating stylet slides out of the endotracheal intubation tube leaving the endotracheal intubation tube in the trachea. Thus, the anesthetist is able to easily handle the integral assembly of a laryngoscope and assembly in the left hand and easily manipulate the endotracheal intubation tube off of the intubating stylet with the right hand.

Another advantage of the present invention is that the intubating stylet can be coated or treated with polytetrafluoroethylene (e.g. Teflon material) or a similar lubricous material.

Another advantage of the present invention is the elongated preformed, relatively rigid elongated member has specially shaped contour such that will conform to a laryngoscope blade, or other insertion member of an instrument.

Another advantage of the present invention is that the elongated stylet is formed into a proximal section and a distal section having a shaped central section extending therebetween. The distal section terminates in a distal tip. In the preferred embodiment, the distal tip is adapted to resiliently removably support the distal end of an endotracheal intubation tube by being passed through the eye thereof located at the distal end, which eye is known in the art as a Murphy's Eye.

Another advantage of the present invention is that the intubating stylet can be either permanently attached to the laryngoscope or can be removably attached thereto.

Another advantage of the present invention is that the intubating stylet includes a connecting means which operatively attaches the intubating stylet to the laryngoscope so that the same is movable therewith. Also, the intubating stylet can be removed from the laryngoscope by means of the connecting means.

Another advantage of the present invention is that the intubating stylet and endotracheal intubation tube can be preassembled, as a subassembly, prior to performing the intubation procedure such as that at the time the intubation procedure is to be performed, the subassembly can be quickly operatively attached to and/or removed from the laryngoscope by a connecting means.

Another advantage of the present invention is that the subassembly comprising the intubating stylet and the endotracheal intubation tube can be easy assembled by passing the distal end of the intubating stylet through the proximal end of the endotracheal intubation tube, through the hollowed out central area extending therethrough and to the distal end of the endotracheal intubation tube passing the distal tip of the distal section of the intubating stylet through the Murphy's Eye wherein the distal tip resiliently removably holds the subassembly together.

Another advantage of the present invention is that it is unnecessary for the anesthetist to manually shape the preformed intubating stylet thereby saving the anesthetist time during the procedure. Also, since the intubating stylet is preshaped, the disadvantages associated with use of malleable stylet are eliminated.

Another advantage of the present invention is that by using a preformed intubating stylet, it is unnecessary for the anesthetist to remove an improperly shaped malleable stylet, reshape the same and then perform the step of reintroducing the same with endotracheal intubation tube into the patient.

Another advantage of the present invention is that by use of a assembly formed of a combination of an intubating stylet and endotracheal intubation tube which is operatively connected to the laryngoscope by a connecting means requires a lessor degree of hand-to-eye coordination than that which is required during the insertion of the intubation tube through the vocal cords into the trachea for using either a malleable stylet or an intubation mechanism of the prior art.

Another advantage of the present invention is that the intubating stylet is operatively connected to the laryngoscope such that removal of the laryngoscope from the patient with intubating stylet operatively connected thereto results in the intubating stylet being easily slidable removed from the endotracheal intubation tube after the same has been positioned in the proper location by the anesthetist.

Another advantage of the present invention is that the laryngoscope, the assembly comprising the intubating stylet and endotracheal intubation tube can be used with a video means as system for generating video images of the intubation procedure.

Another advantage of the present invention is that a new and novel method for intubating a patient is disclosed using the intubating stylet disclosed herein.

BRIEF DESCRIPTION OF THE DRAWINGS

These and other advantages of the invention will be readily apparent when considered in light of the detailed description hereinafter of the preferred embodiment and of the drawings which include the following figures.

DESCRIPTION OF THE PREFERRED EMBODIMENT

Before commencing with the details of the preferred embodiment, it would helpful to describe the prior art intubation mechanism which is adapted to be operatively connected to a laryngoscope for supporting and directing an endotracheal intubation tube into the trachea of a patient.

Figure 1:
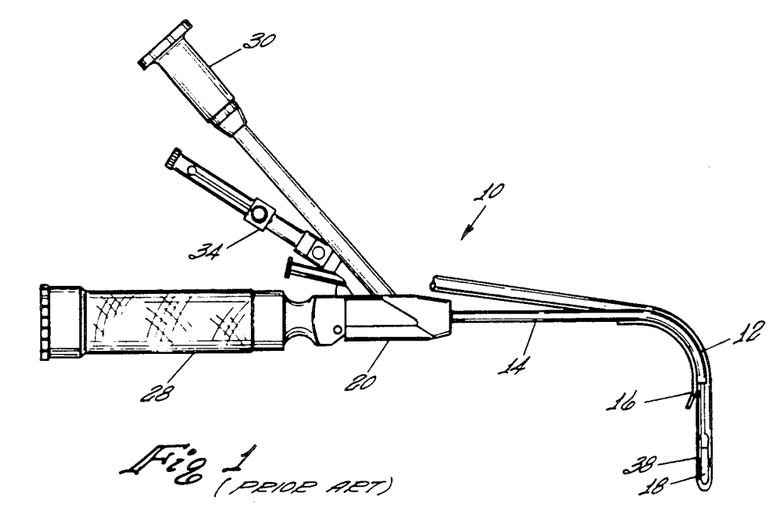
FIG. 1 is a sideplan view of a laryngoscope of the prior art having an intubation mechanism and an endotracheal intubation tube operatively attached to the laryngoscope and supported by the jaws of the intubation mechanism.

FIG. 1 (labelled Prior Art) is a front view of a laryngoscope 10 which is intended to be used for inserting an endotracheal intubation tube 12 into the trachea of a patient. Laryngoscope 10 has a frame 14 which supports a relatively rigid blade 16 of a curved figuration which is anatomically shaped to be inserted into the mouth or oral cavity of a patient. The blade 16 is formed of a suitable material such as metal or plastic. The blade 16 of the laryngoscope has a curved insertion member which is adapted to be inserted into a patient's mouth. The proximal end of the frame 14 is operatively connected to a control head 20.

Figure 11:
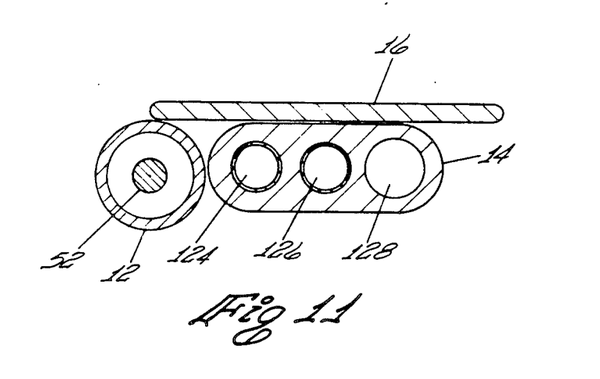
FIG. 11 is a sectional view taken along section lines 11—11 of FIG. 2 showing the relationship between the working channel, a channel enclosing the fiber optic image bundle, a channel enclosing the light bundle and the subassembly formed of an intubating stylet and endotracheal intubation tube.

The control head 20 comprises four main sections: a handle/battery section 28, a fiber optic image bundle (shown as 126 in FIG. 11), a working channel (shown as 128 in FIG. 11) and a fiber light guide (shown as 124 in FIG. 11). The intubation mechanism 34 includes a grasping and extension control. The extension control performs the functions of grasping and extending the length of the blade 16 as illustrated by the extended grasping means 38 which functions to grasp the endotracheal intubation tube 12 proximate a Murphy's Eye 18 located in the periphery of the endotracheal intubation tube 12. The grasping means 38 is utilized to direct the distal tip of the endotracheal intubation tube 12 through the larynx and into the trachea of a patient.

In the prior art, the intubation mechanism 34 is provided to manually advance the grasping means 38 which is operatively connected to the Murphy Eye 18 of the endotracheal intubation tube 12 and to open and close the jaws of the grasping means 38 to permit the endotracheal intubation tube to be manually advanced by the anesthetist through the larynx and into the trachea of the patient.

As described herein before, the anesthetist must have a high degree of manual dexterity and good hand-to-eye coordination to pass the distal end of the endotracheal intubation tube 12 through the vocal cords and into the trachea of a patient.

The present invention replaces the need for an intubation mechanism 34 including the grasping means 38 thereof. The prior art intubation mechanism 34 has an elongated shaft which is positioned with and occupies the working channel of the laryngoscope frame 14 (or core) which defines a support for the curved blade 16. FIG. 11 illustrates a sectional view of the frame 14 (or core) of the laryngoscope 10 which supports the curved blade 16. When the working channel is occupied by the intubating mechanism, it cannot be used for other functions such as applying a suction or oxygenation through a luer lock to the working channel shown as 128 in FIG. 2.

Figure 2:
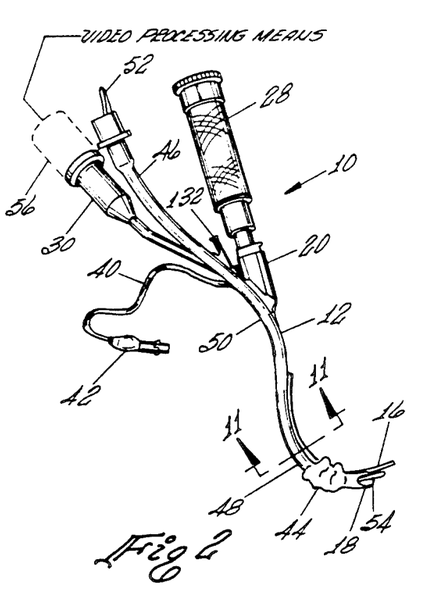
FIG. 2 is a side plan view of a laryngoscope of FIG. 1 having attached thereto a subassembly formed of a intubating stylet and an endotracheal intubation tube.
Figure 3:
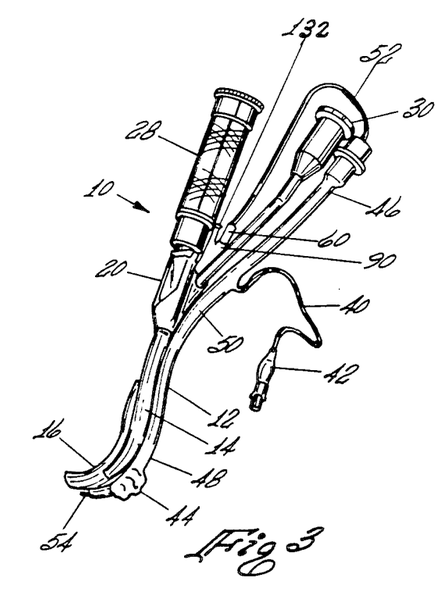
FIG. 3 is a rear prospective view of the laryngoscope of FIG. 2 showing the location of the intubating stylet having the endotracheal intubation tube mounted thereon which, in turn, is operatively attached to the laryngoscope by means of a connecting means.

FIGS. 2 and 3 show a laryngoscope 10 having a shaped frame 14 with a relatively rigid blade 16 together with an intubating stylet 52 operatively connected thereto. The intubating stylet 52 is used to position a workpiece, such as for example the endotracheal intubation tube 12 in the larynx and upper tracheal region of the larynx. This is discussed in greater detail in connection with FIGS. 14(A), 14(B) and 14(C).

Referring again to FIGS. 2 and 3, a typical endotracheal intubation tube 12 has a proximal end 46, a distal end 48 and thin wall tube defining a hollowed out central area extending axially therethrough shown generally as 50, extends from the proximal end 46 to the distal end 48. In one known endotracheal intubation tube, the distal end 48 includes an opening 18 which extends through the tube wall 50, which opening 18 is generally known as a Murphy's Eye.

In the preferred embodiment, the endotracheal intubation tube 12 includes a inflatable sealing means 44 located near the distal end 48 of the endotracheal intubation tube 12. The inflatable sealing means functions as a sealing means to maintain the anesthesia gases within the lungs of a patient. A means for inflating the sealing means 40 includes a flexible tube 40 which extends from the sealing means 40 to the inflatable sealing means 44. Also, a video means 56 may be operatively connected to the eyepiece 30 to receive the optical image. Video processing means operatively connected to the video means 56 can be used to develop and display or record a video image of the transmitted optical image.

It is also envisioned that an endotracheal intubation tube could be used with the intubating stylet of the present invention without an opening 18 and without an inflatable sealing means 44.

FIG. 3 shows that the proximal end (shown as 66 in FIG. 4) of the intubating stylet 52 is operatively connected to a connecting means 60 which, in turn, is removably attached to a housing boss 90 (shown in FIGS. 8, 9 and 10) to operatively attach the intubating stylet 52 to laryngoscope 10 such that the intubating stylet 52 is removable therewith. In the alternative, intubating stylet 52 may be operatively attached to the laryngoscope by a permanent attached means.

Figure 4:
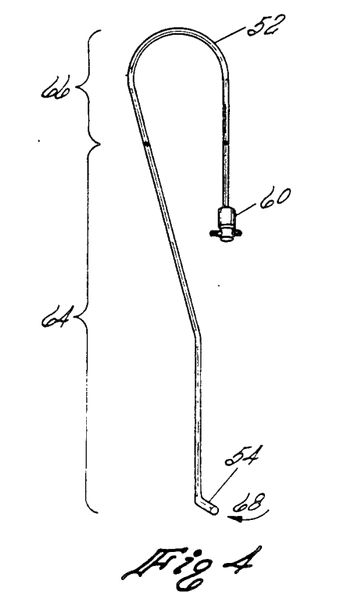
FIG. 4 is a front plan view of the preformed intubating stylet showing a proximal section, a distal section and a shaped central section extending therebetween and wherein the proximal section terminates in a connecting means and the distal section terminates in a distal tip.
Figure 5:
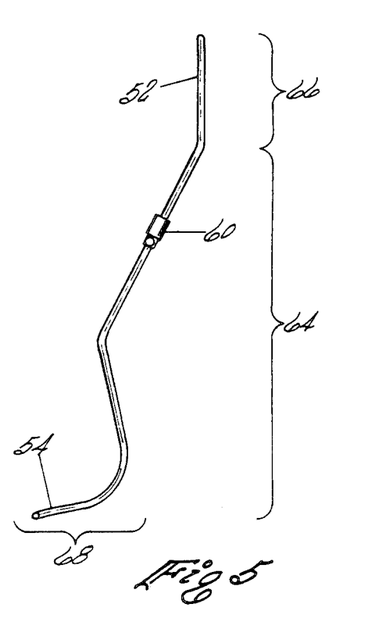
FIG. 5 is a right side plan view of the intubating stylet of FIG. 4.

FIGS. 4 and 5 show in detail the structure of the intubating stylet 52. Specifically, the intubating stylet 52 is a preformed relatively rigid elongated member having a central portion 64, a proximal portion 66 and a distal portion 68. The central portion 64 extends between the proximal portion 66 and the distal portion 68. The elongated member is contoured from the central section 64 to the distal section 68 to substantially follow the shape of the shaped frame 14 and the rigid blade 16 as shown in FIGS. 2 and 3. The distal portion 68 terminates in a distal tip 54 which, in the preferred embodiment, has a lateral bend of approximately 15° to about 30°. However, it is not essential that the distal tip 54 have a lateral bend to practice this invention. The elongated member is contoured from the central section 64 to proximal portion 66 to substantially follow the shape of the laryngoscope and extends in a direction opposite to the relatively rigid blade 16. In the embodiment illustrated in FIGS. 4 and 5, the proximal portion 66 then reverses itself in a "U" shape end and extends back towards the rigid blade 16 to enable the connecting means 60, connected to one leg of the "U" shaped end, to be operatively connected to a raised boss member 90 (shown in FIGS. 9 and 10) such that the intubating stylet 52 is movable with the laryngoscope 10. The other leg of the "U" shaped end is connected to the proximal section 66 of the laryngoscope.

In the embodiment of the intubating stylet 52 depicted in FIGS. 4 and 5, the intubating stylet 52 may be coated with a lubricous material such as, for example, a medical grade lubricant. The lubricant could be, for example, a medical grade silicone or polytetrafluoroethylene, such as a Teflon coating. Preferably, the rigid intubating stylet is formed of a rigid material, such as for example stainless steel or rigid plastic. The intubating stylet is shaped to accommodate a commercially available endotracheal intubation tube such as, for example, an endotracheal intubation tube offered for sale and sold by Ohio Medical. However, other endotracheal intubation tubes of different construction may be used with the intubating stylet.

The proximal portion 66 of the intubating stylet 52 has the length of approximately three inches (about 7.6 cm). The diameter of the "U" shaped end has a diameter of approximately 2.5 inches (about 6.4 cm). The central section is approximately 10.5 inches (about 26.7 cm) along the vertical dimension as shown by bracket 64. The distal portion 54 is approximately 3 inches (about 7.6 cm) in length as shown by bracket 68 in FIG. 5. The distal tip 54 is bent laterally towards connecting means 60 preferably about 25°. Also, it is envisioned that the distal tip could be a semi-flexible tip or an interchangeable tip and could be formed into a suitable guide element, e.g. ball shaped member to avoid injury to a patient.

Figures 6, 7:
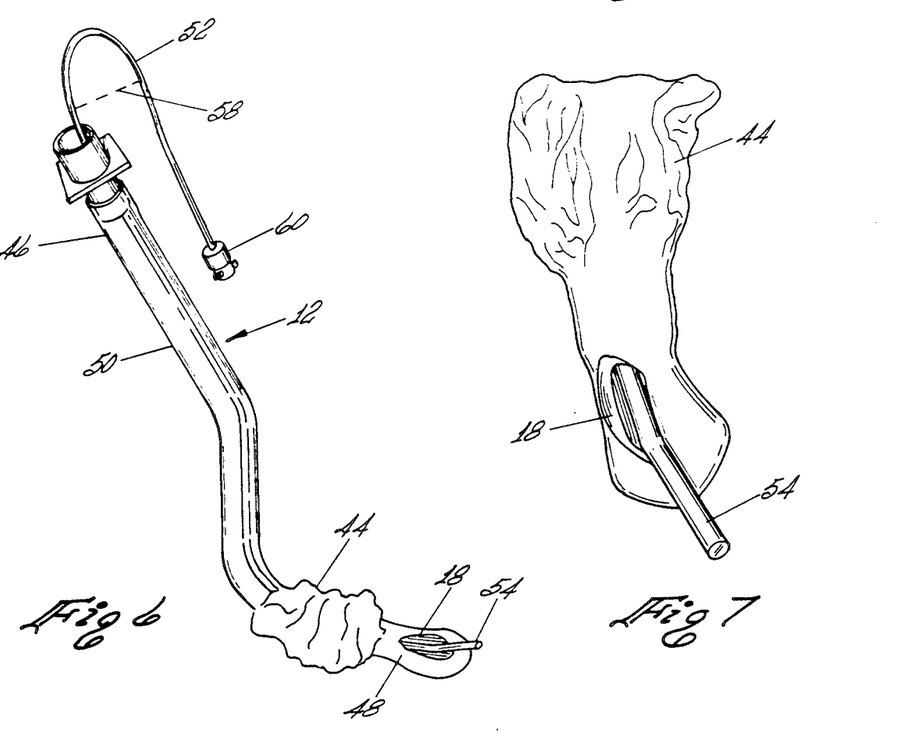
FIG. 6 is a perspective pictorial representation of a subassembly formed of the intubating stylet and an endotracheal intubation tube wherein the distal tip of the intubating stylet resiliently removably holds the endotracheal intubation tube in position by passing the distal tip through the Murphy's Eye of the endotracheal intubation tube.
FIG. 7 is a pictorial representation of the distal end of an endotracheal intubation tube having the intubating stylet distal tip having a lateral bend passing through the Murphy's Eye which slightly compresses the distal end of the endotracheal intubation tube to resiliently clamp the same.

FIG. 6 illustrates a subassembly comprising an endotracheal intubation tube 12 having a proximal end 46, a distal end 48 and a thin wall tubing defining a hollowed out central area 50 extending axially therethrough and through the proximal end 46 and the distal end 48.

In the preferred embodiment, the distal end 48 includes the Murphy's Eye 18 which extends through the tube wall 50. The intubating stylet 52 extends axially through the hollowed out central area of wall 50. Specifically, the preformed intubating stylet 52 when loaded with the endotracheal intubation tube 12 has the proximal section 66 extending beyond the proximal end 46 thereof. The elongated member central section 64 is enclosed by the hollowed out central area defined by wall 50 with the distal portion 68 which terminates in a distal end 54 having a lateral bend which extends through the opening 18.

The proximal portion 66 which terminates, in the preferred embodiment, in the connecting means 60 which is used for operatively connecting the intubating stylet 52, having the endotracheal intubation tube 12 attached thereto to the laryngoscope 10 so as to be movable therewith. As is illustrated in FIG. 6, the intubating stylet 52 passes axially through the hollowed out central area 50 with the distal end 68 positioned to pass through the opening 18 in the endotracheal intubation tube 12. The distal tip 54 having the lateral bend is passed through the opening 18 enabling the distal tip 54 to resiliently removably clamp the distal end 48 of the endotracheal intubation tube 12 against the intubating stylet 52 forming an integral subassembly of the intubating stylet 52 and the endotracheal intubation tube 12. If desired, the degree of movement and/or stiffness of the intubating stylet can be controlled by the addition of a stiffening means or clamping means 58, which may be an adjustable or fixed clamp.

FIG. 7 is a pictorial representation of the relationship between the distal tip 54 having a lateral bend as it is passed through the Murphy's Eye opening 18 at the distal end 48 of endotracheal intubation tube 12. As shown by FIG. 7, the distal section 48 of tube 12 is resiliently removably held against the intubating stylet 52 forming an integral subassembly. An important feature of the structure illustrated in FIG. 7 is that an anesthetist can very easily apply a downward force or pushing force of an appropriate magnitude to the proximal end 46 of the endotracheal intubation tube 12 to cause the opening 18 to be pushed off of the distal end 54 of the intubating stylet 52 such that the distal end 48 of the endotracheal intubation tube 12 easily slides off of the intubating stylet 52 and is guidingly urged through the larynx (vocal cords) and into the trachea of a patient. In the alternative, if the distal tip 54 is not passed through the Murphy's Eye, the force required to slide the endotracheal intubation tube off of the intubating stylet is the force required to overcome the function between the inner wall of the wall 50 and the intubating stylet 52.

Figure 8:
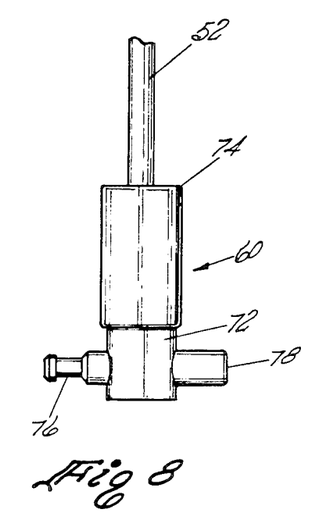
FIG. 8 is a front plan view of the proximal section of the intubating stylet which is operatively attached to a connecting means, which connecting means is adapted to be removably connected to a connecting boss located on the laryngoscope.

FIG. 8 illustrates in greater detail the structure of the preferred embodiment of the connecting means 60 which is operatively connected to the proximal end 66 of the intubating stylet 52. The connecting means 60 includes a body 72 which has mounted on one side thereof a hollowed out pin 78 enclosing a spring and on the other side thereof and in an opposed lateral position, a plunger member which is spring loaded by the spring enclosed in the opposed hollowed out pin 78. The plunger member includes a raised collar which functions as a locking mechanism for the operating connecting means 60. The housing 72 includes an extended member 74 which is operatively connecting to the proximal end 66 of the intubating stylet 52.

Figure 9:
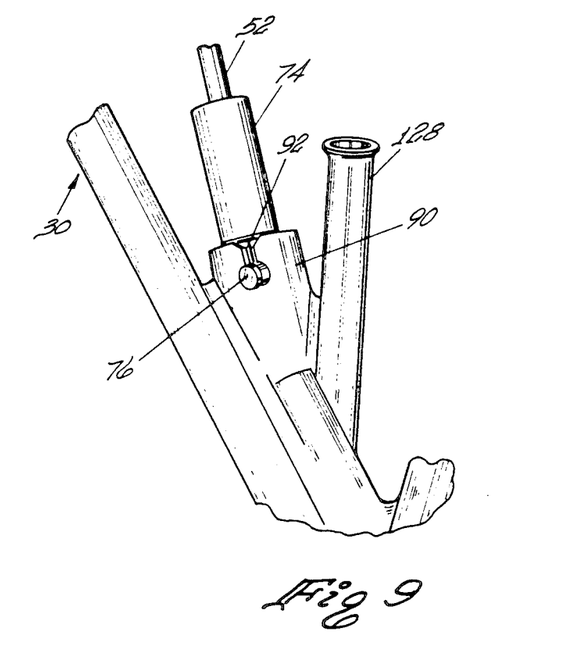
FIG. 9 is a partial front plan view showing the connecting means having the proximal section of the intubating stylet extended therefrom being operatively connected to the connecting boss located on an endoscope.

FIG. 9 illustrates pictorially the connecting means 60 in the connecting position with a raised boss member 90 located on the laryngoscope 10. The body 72 of the connecting means 60 is dimensioned to slide into a hollowed out opening in the boss member 90. The boss member 90 includes slotted apertures 92 which are adapted to receive and cooperate with the hollowed out pin member 78 and the plunger member 76. The diameters of the openings at the lower end of the slotted apertures 92 are sized to accommodate the appropriate diameter of members 76 and 78.

As illustrated in FIG. 9, the plunger member 76 includes a locking member 94 (shown in FIG. 10) having a diameter which enables the plunger member 76 to be extended to a locking position under a springloaded arrangement. When locking member 94 is in a locking position, the connecting means 60 is retained within the boss 90 such that the intubating stylet 52 is operatively connected to the laryngoscope 10 so as to be movable therewith. Also, the entrance to the working channel 128 is shown. The working channel can be used for applying a suction to the trachea or for passage of other workpieces or tools.

Figure 10:
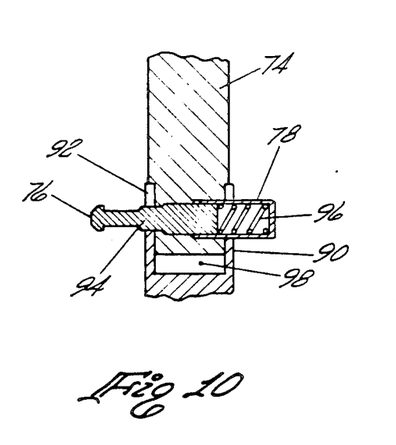
FIG. 10 is a partial cross sectional view showing the operative relationship between the connecting means and the connecting boss located on a laryngoscope.

FIG. 10 shows in greater detail, by cross section view, the relationship between the boss member 90, the hollowed out pin 78 and the plunger member 76. The body 72 of the connecting means 60 is dimensioned to be inserted into and positioned within a hollowed out central area 98 in boss member 90. The locking member 94 cooperates with slot 92 to lock the body 72 within the boss member 90. The elongated extended member 74 is operatively connected to the proximal end 66 of the intubating stylet 52.

FIG. 11 illustrates a pictorial representation of a section of the frame 14 (or core) of the laryngoscope 10 which supports the curved blade 16. In FIG. 11, the fiber optic image bundle is shown as 126, the light guide is shown as 124 and the working channel is shown as 128.

FIG. 11 depicts the location of the endotracheal intubation tube 12 mounted on the intubating stylet 52 which are held against the frame 14 and under the edge of the curved blade 16 due to the shape of the intubating stylet 52. The shape of the intubating stylet 52 applies a slight resilient clamping action against the frame 14 of the laryngoscope 10. The stiffness of the clamping action may be controlled by a clamping means 58 as shown in FIG. 6.

Figures 13, 14A, 14B, 14C:
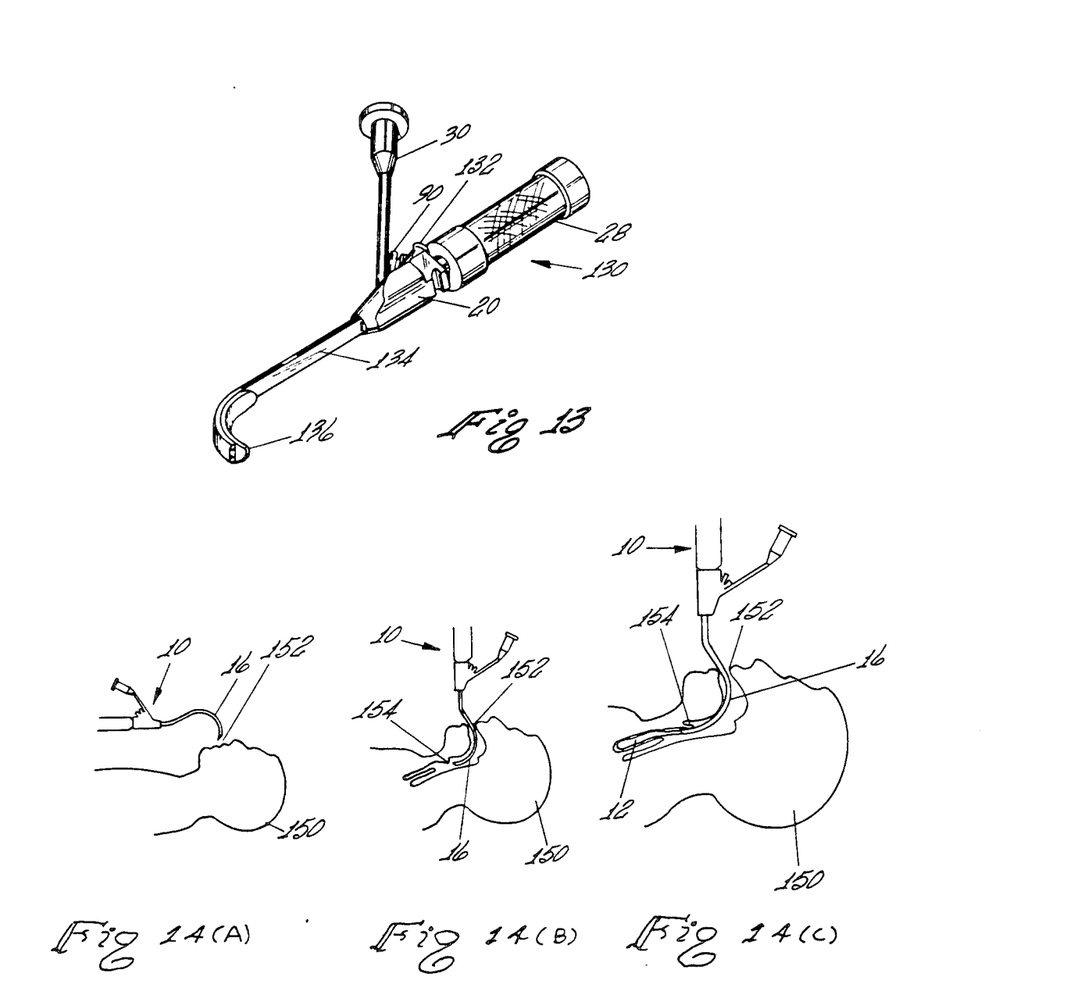
FIG. 13 is a front plan view of another embodiment of an endoscope utilized for pediatric procedure wherein a subassembly formed of an intubating stylet and an endotracheal intubation tube adapted to be operatively attached either by a permanent attachment of a connecting means to another embodiment of a laryngoscope.
FIGS. 14(A), 14(B) and 14(C) represent the steps of a method for oral introduction and placement of a laryngoscope having the subassembly form of the intubating stylet and the endotracheal intubation tube operatively attached thereto in the trachea of a patient.

FIG. 13 is a representation of yet another embodiment of a laryngoscope shown generally as 130. The laryngoscope shown in FIG. 15 is of a size and shape to be utilized in a pediatric application. The structure and relationship is such that the laryngoscope control head 20, eyepiece 30 and other structure includes a luer lock 132 which is operatively coupled to the working channel 128 and which is substantially of the same construction as that of the laryngoscope 10 illustrated in FIGS.

2 and 3. However, the frame 134 is of a smaller diameter and terminates in a smaller, less curved blade structure 136. The blade structure 136 is located at a substantially right angle to the frame 134 so as to conform with the small dimensions associated with a child for which the pediatric laryngoscope 134 can be used. The physical sizes of the intubating stylet 52 and the endotracheal intubation tube 12 used for pediatric application would be appropriately sized. The intubating stylet may be permanently attached to the laryngoscope of FIG. 13 rather than using a connecting means 60. Also, in this application, an endotracheal intubation tube not having a Murphy's Eye may be used.

Typically, the cross sectional dimension of the elongated member defining the intubating stylet 52 for an adult laryngoscope 52 would have a diameter in the order of 3.5 mm to about 4.00 mm. In a pediatric laryngoscope, the cross sectional dimension of the intubating stylet would be in the order of about 2.5 mm to about 3.0 mm.

The cross sectional dimension of a typical endotracheal intubation tube for an adult laryngoscope would be in the order of about 7 mm to 10 mm. A cross sectional diameter of an endotracheal intubation tube for a pediatric application would be in the order of about 3 mm to about 5 mm.

Figure 12A:
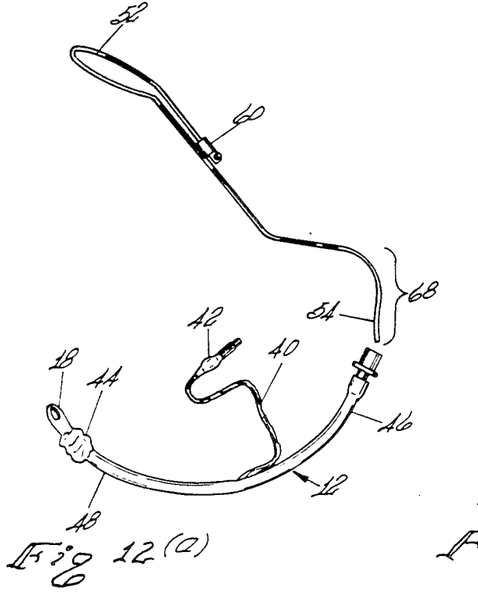
FIG. 12(A) illustrates the positioning of the distal end of the intubating stylet relative to the proximal end of the endotracheal intubation tube prior to forming the subassembly.

FIGS. 12(A), 12(B), 12(C) and 12(D) show a method for forming the subassembly formed of an intubating stylet 52 and an endotracheal intubation tube 12. In FIG. 12(A), the intubating stylet 52 is position such that the distal portion 68 thereof is positioned to direct the distal tip 54 through the proximal end 46 of the endotracheal intubation tube 50.

Figure 12B:
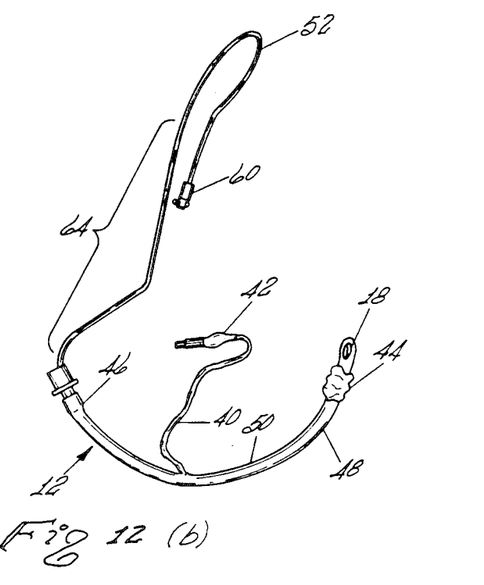
FIG. 12(B) illustrates the distal section of the intubating stylet being passed through the proximal end of the endotracheal intubation tube so as to advance the distal tip thereof through the hollowed out central area thereof.

FIG. 12(B) illustrates that the distal section 68 has been transported partially into the endotracheal intubation tube 12.

As shown in FIG. 12(B), the central portion 64 of the intubating stylet 52 is the next portion of the intubating stylet 52 which is passed through the endotracheal intubation tube 12.

Figure 12C:
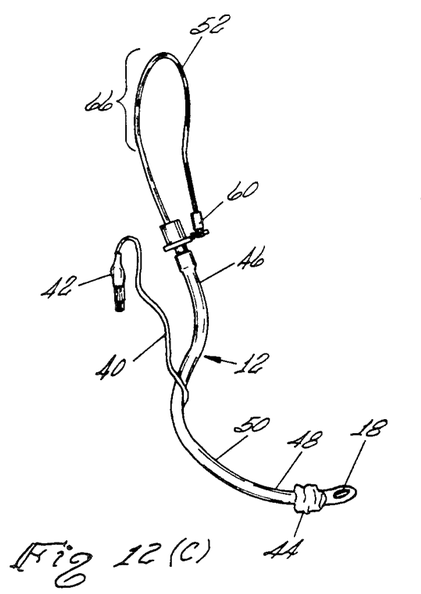
FIG. 12(C) illustrates the central portion of the intubating stylet being passed through the proximal end of the endotracheal intubation tube advancing the distal tip into the distal region of the endotracheal intubation tube, and 12(D) illustrates the subassembly formed of the intubating stylet having the endotracheal intubation tube operatively connected thereto by means of the distal tip of the intubating stylet passing through the Murphy Eye of the endotracheal intubation tube so as to removably resiliently support the endotracheal intubation tube in position with the intubating stylet extending through the hollowed out central area of the endotracheal intubation tube.

FIG. 12(C) shows that the endotracheal intubation tube 12 has been advanced further onto the preformed intubating stylet 52 such that the distal section 68 and the central section 64 of the intubating stylet 52 has been advanced axially within the hollowed out central area of wall 50 of the endotracheal intubation tube 12.

Figure 12D:
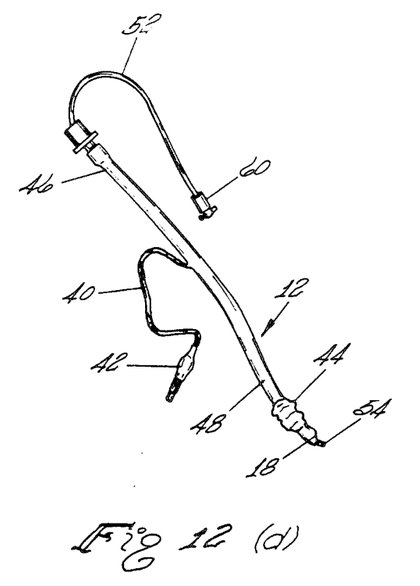

FIG. 12(D) shows the final step for forming the subassembly wherein the endotracheal intubation tube 12 is transported to the point where the distal section 64 of the intubating stylet 52 is located relative to the distal section 48 of the endotracheal intubation tube 12 such that the distal tip 54 of the intubating stylet 52 can, if desired, be passed through the opening 18 and to apply a resilient removable clamping action thereagainst. The clamping action of the laterally bent distal tip 54 functions to further hold the assembly together (along with the friction between the stylet 52 and tube 12) as integral unit. However, the amount of the clamping force generated by the lateral bend in the end of the distal tip 54 which results in a resilient force being urged against the exterior of the endotracheal intubation tube distal section 48 can be easily overridden by the anesthetist applying, on the external wall of the endotracheal intubation tube 12, an appropriate magnitude of driving or pushing force along the axis of the intubating stylet in the direction towards the distal end 48 of the endotracheal intubation tube, which pushing force would be of sufficient force to slide the opening 18 off of the distal tip 54 (if the distal tip 54 is passed through the opening 18) and into the trachea as described in greater detail in connection with FIGS. 13(A), 13(B) and 13(C).

In order to aid in both the assembly of the subassembly as described in connection with FIGS. 12(A), 12(B), 12(C) and 12(D) and the removal of the tube 12 therefrom during the intubation procedure, a silicon lubricant or other appropriate medical grade lubricant can be applied to the exterior of the intubating stylet 52 so as to make relative movement between the intubating stylet 52 and the interior walls of tube 50 of the endotracheal intubation tube 12 as smooth and as easy as possible and to reduce friction.

Specifically, the use of a silicon or other type of lubricant as described hereinabove makes it easier for the anesthetist to slide the endotracheal intubation tube 12 off of the intubating stylet 52 and into the trachea.

FIGS. 14(A), 14(B) and 14(C) illustrate the steps utilized for the oral introduction and placement of the endotracheal intubation tube 12 within the patient. FIG. 14(D) shows that the patient 150 is position in a supine position such that the oral cavity or mouth 152 is directed towards the user. The laryngoscope 10 having a subassembly comprising the intubating stylet 52 and endotracheal intubation tube 12 operatively connected thereto is positioned as illustrated in FIG. 14(A) with the handle substantially parallel to the chest of the patient and position such that the rigid blade 16 and subassembly are adapted to be inserted into the mouth 152.

FIG. 14(B) shows that the laryngoscope including the subassembly of the intubating stylet 52 and endotracheal intubation tube 12 affixed thereto is then essentially rotated 90° from the horizontal to vertical position positioning the anatomically shaped blade 16 to enter the mouth 152 and slide around the tongue. Once the laryngoscope 10 is fully vertical, final placement of the blade 16 may be facilitated by allowing the blade 16 to drop momentarily to the posterior pharynx and adjacent the epiglottis 154.

FIG. 14(C) shows that the blade 16 is then elevated against the tongue's dorsal surface. Only minimal upward movement need be exerted along the axis of laryngoscope 10 which results in the tip of the blade 16 being used to lift the epiglottis 154. The anesthetist then applies a drive or pushing force on the endotracheal intubation tube 12 to transport the same off of the intubating stylet 52 and into the trachea.

In order to remove the laryngoscope 10 having the intubating stylet 52 operatively connected thereto by connecting means 60, the anesthetist reverses the above described procedure. In the removal procedure, the assembly formed of the laryngoscope 10 and intubating stylet 52 operatively connected to the laryngoscope 10 can be held by the anesthetist with one hand in that the intubating stylet 52 easily slides out of the proximal end 46 of the endotracheal intubation tube.

Although the preferred embodiment disclosed herein is an adult size laryngoscope adapted for intubating an adult patient, it is apparent from the description herein that a pediatric laryngoscope, such as for example the pediatric laryngoscope as illustrated in FIG. 13 hereof, can utilize a similar structure which comprises of an appropriately sized preformed intubating stylet. Also, any type of instrument which includes an insertion member, such as any other type of laryngoscope having an anatomically shaped blade, could likewise use the teachings of the present invention.

It is also within the teachings of the present invention to utilize a video means (as shown by dashed element 56 in FIG. 2) which is operatively connected to the eyepiece 30 of the laryngoscope 10 as disclosed herein. The video means is operatively connected to a video processing system which produces a video image. In operation, the video means 56 receives the optical image which is transmitted by the fiber optic image bundle from the working site within the human body, such as in the area of the larynx or vocal cords, to the eyepiece. The anesthetist can then have visual confirmation, by viewing the video image, that the endotracheal intubation tube has been smoothly slidably transported from the intubating stylet, past the larynx and into the trachea of a patient.

What is claimed is:

1. A laryngoscope having a shaped frame with a relatively rigid blade and an intubating stylet operatively coupled thereto for positioning a workpiece in the larynx and upper tracheas region of a patient, said intubating stylet comprising
a relatively rigid performed elongated member having a distal section, a proximal section and a central section extended therebetween, said proximal section having a "U" shaped end having two legs wherein one leg of the "U" shaped end is operatively connected with the central section and wherein the central section extends at an angle away from a plane defined by the legs of the "U" shaped end and wherein the distal section extends away from the central section at an angle and towards the "U" shaped end, and wherein said distal section terminates in a distal tip.

2. The laryngoscope of claim 1 wherein said proximal portion terminates in a connecting means for operatively coupling said intubating stylet to the laryngoscope so as to be moveable therewith.

3. The laryngoscope of claim 1 wherein said intubating stylet is permanently attached to said laryngoscope.

4. The laryngoscope of claim 1 wherein the other leg of said "U" shaped end is operatively connected to a connecting means adapted to be removably connected to said laryngoscope.

5. The laryngoscope of claim 4 wherein said distal tip has lateral bend of about 15° in a direction towards said connecting means for removably supporting a workpiece.

6. The laryngoscope of claim 1 wherein the diameter of said "U" shaped end is about 2.5 inches.

7. A laryngoscope having a shaped frame, a working channel, a fiber optic image channel, a light guide channel and a relatively rigid blade, said laryngoscope including an intubating stylet operatively coupled thereto for positioning an endotracheal intubation tube in the larynx and upper tracheas region of a patient, said intubating stylet comprising
a relatively rigid elongated member having a central portion, a proximal portion and a distal portion, said elongated member being contoured from said central section to said distal section to substantially follow the shape of the shaped frame and rigid blade, said distal portion terminating in a distal tip, said elongated member being contoured from said central section to said proximal portion to substantially follow the shape of the laryngoscope which extends in a direction opposite to the relatively rigid blade, said proximal portion having a "U" shaped end having two legs, one of which is operatively coupled to said central section and extends away from a plane defined by the legs of the "U" shaped end and wherein the other leg terminates in a connecting means for operatively coupling said intubating stylet to the laryngoscope so as to be moveable therewith.

8. The laryngoscope of claim 7 wherein said distal tip has a lateral bend which is about 15° and in a direction towards said connecting means.

9. An intubating stylet adapted to be operatively connected to a laryngoscope having a shaped frame with a relatively rigid blade for positioning a workpiece in the larynx and upper tracheas region of a patient, said intubating stylet comprising
a relatively rigid elongated member having a central portion, a proximal portion and a distal portion, said proximal portion having a "U" shaped end having two legs wherein one leg of the "U" shaped end is operatively connected with the central section and wherein the central section extends at an angle away from a plane defined by the legs of the "U" shaped end and wherein the distal section extends away from the central section at an angle and towards the "U" shaped end, and wherein said distal portion terminates in a distal tip, said other leg of the "U" shaped end terminating in a connecting means for operatively coupling said intubating stylet to the laryngoscope so as to be moveable therewith.

10. An intubating stylet for use with an intubating instrument having an insertion member comprising
a relatively rigid elongated member having a central portion, a proximal portion and a distal portion, said proximal portion having a "U" shaped end having two legs wherein one leg of the "U" shaped end is operatively connected with the central section and wherein the central section extends at an angle away from a plane defined by the legs of the "U" shaped end and wherein the distal section extends away from the central section at an angle and towards the "U" shaped end, and wherein said distal portion terminates in a distal tip, said other leg of said "U" shaped end terminating in a connecting means for operatively coupling said intubating stylet to the intubating instrument so as to be moveable therewith.

11. A subassembly comprising
an endotracheal intubation tube having a proximal end, a distal end and a hollowed out central area extending axially therethrough and through said proximal end and said distal end; and
an intubating stylet comprising
a relatively rigid elongated member having a central portion, a proximal portion and a distal portion, said proximal portion having a "U" shaped end having two legs wherein one leg of the "U" shaped end is operatively connected with the central portion and wherein the central portion extends at an angle away from a plane defined by the legs of the "U" shaped end and wherein the distal portion extends away and from the central section at an angle and towards the "U" shaped end, and wherein said distal portion terminates in a distal tip, said other leg of the "U" shaped end terminating in a connecting means for operatively coupling said intubating stylet to an intubating instrument so as to be moveable therewith, said elongated member being contoured to pass axially through the hollowed out central area with the distal tip extending to about the distal end of said endotracheal intubation tube.

12. In combination
a laryngoscope having a shaped frame with a relatively rigid blade for positioning a workpiece in the larynx and upper tracheas region of a patient;
an endotracheal intubation tube having a proximal end, a distal end and a thin wall defining a hollowed out central area extending axially therethrough and through said proximal end and said distal end;
an intubating stylet comprising
a relatively rigid elongated member having a central portion, a proximal portion and a distal portion, said proximal portion having a "U" shaped end having two legs wherein one leg of the "U" shaped end is operatively connected with the central portion and wherein the central portion extends at an angle away from a plane defined by the legs of the "U" shaped end and wherein the distal section extends away from the central section at an angle and towards the "U" shaped end, and wherein said distal portion terminates in a distal tip and wherein the other leg of said "U" shaped end terminates in a connecting means for operatively coupling said intubating stylet to an intubating instrument so as to be moveable therewith, said elongated member being contoured to pass axially through the hollowed out central area with the distal tip passing through said endotracheal intubation tube to about the distal section thereof.

13. A method for forming a subassembly having an intubating stylet and an endotracheal intubation tube comprising the steps of
positioning a relatively rigid, preformed intubating stylet which has an elongated member having a central portion, a proximal portion and a distal portion, said proximal portion having a "U" shaped end having two legs wherein one leg of the "U" shaped end is operatively connected with the central section and wherein the central section extends at an angle away from a plane defined by the legs of the "U" shaped end and wherein the distal section extends away from the central section at an angle and towards the "U" shaped end, and wherein said distal portion terminates in a distal tip which is directed through an endotracheal intubation tube having a proximal end, a distal end and a thin wall tube defining a hollowed out central area wherein the distal portion of the intubating stylet is passed through to the proximal end of the endotracheal intubation tube;
transporting the central portion of the intubating stylet through the proximal end of the endotracheal intubation tube directing the distal tip of the intubating stylet towards the distal end of the endotracheal intubation tube; and
transporting the proximal section of the intubating stylet to a point where the distal section of the intubating stylet is located relative to the distal section of the endotracheal intubation tube.

14. The method of claim 13 comprising the additional step of applying a lubricous material on the surface of the intubating stylet before positioning the distal section thereof in the proximal end of the endotracheal intubation tube.

15. The method of claim 13 wherein said distal tip has a lateral bend formed therein and the distal end of the endotracheal intubation tube includes an opening and wherein said step of passing the distal tip through the opening further comprising the step of passing the lateral bend of the distal tip through said opening.

16. The method of intubating a patient having an oral cavity, a tongue having a dorsal surface, a posterior pharynx, a larynx, an epiglottis and an upper trachea comprising the steps of
positioning the patient in a supine position wherein the oral cavity is accessible for intubation;
positioning in a horizontal position a laryngoscope having an assembly operatively attached thereto wherein the laryngoscope includes a shaped frame with a relatively rigid, anatomically shaped blade for positioning a workpiece in the larynx and upper tracheas region of a patient and wherein the assembly comprises a relatively rigid preformed intubating stylet which has an elongated member having a central portion, a proximal portion and a distal portion and wherein said elongated member is contoured from said proximal section to said distal section and wherein said distal section terminates in a distal tip which extends axially through an endotracheal intubation tube having a proximal end, a distal end and a thin wall tube defining a hollowed out central area and wherein the intubating stylet is positioned in the thin wall tube such that the distal tip of said intubating stylet positioned within about this distal end of the endotracheal intubation tube such that the anatomically shaped blade and assembly are located at and adapted to be passed into the oral cavity;
rotating the laryngoscope and assembly as an integral unit about 90° from the horizontal portion to a vertical position positioning and moving the anatomically shaped blade to enter into the oral cavity and slidably around the tongue of a patient;
permitting the blade to drop momentarily to the posterior pharynx and adjacent the epiglottis;
applying a driving force on the exterior of the endotracheal intubation tube having sufficient magnitude to slide the distal end off of the distal tip of said intubating stylet; and
directing the distal end of the endotracheal intubation tube past the larynx and into the upper tracheas region of a patient.

17. The method of claim 16 further comprising the step of
rotating the laryngoscope and the intubating stylet from the vertical position about 90° and in the direction towards the original horizontal position withdrawing the anatomically shaped blade and distal end of the intubating stylet from the oral cavity of a patient.

18. A system comprising
a laryngoscope having a shaped fiber optic image bundle communicating with an eyepiece, a light guide, and frame with a relatively rigid blade for positioning a workpiece in the larynx and upper trachea of a patient;
a relatively rigid, preformed intubating stylet having an elongated member including a central portion, a proximal portion and a distal portion, said proximal portion having a "U" shaped end having two legs wherein one leg of the "U" shaped end is operatively connected with the central section and wherein the central section extends at an angle away from a plane defined by the legs of the "U" shaped end and wherein the distal section extends away from the central section at an angle and towards the "U" shaped end, and wherein said distal section terminates in a distal tip;

an endotracheal intubation tube having a proximal end, a distal end and a thin wall tube defining a hollowed out central area; and a video means including a video processing means operatively coupled to the eyepiece of the laryngoscope for processing a video image of an optical image transmitted to the eyepiece by the fiber optic image bundle.

19. A subassembly comprising an endotracheal intubation tube having a proximal end, a distal end and a hollowed out central area extending axially therethrough and through said proximal end and said distal end and wherein said endotracheal intubation tube further includes an opening located in the distal end of said endotracheal intubation tube which is adapted to have the distal tip of the intubating stylet pass therethrough, said endotracheal intubation tube further including an inflatable sealing means located near the distal end of said endotracheal intubation tube;

means for inflating said sealing means operatively connected to said inflatable sealing means; and an intubation stylet comprising a relatively rigid elongated member having a central portion, a proximal portion and a distal portion, said elongated member being contoured from said proximal section to said distal section and wherein said distal portion terminates in a distal tip, said proximal portion terminating in a connecting means for operatively coupling said intubating stylet to an intubating instrument so as to be moveable therewith; said elongated member being contoured to pass axially through the hollowed out central area with the distal tip extending to about the distal end of said endotracheal intubation tube.

20. A method for forming a subassembly having an intubating stylet and an endotracheal intubation tube comprising the steps of positioning a relatively rigid, preformed intubating stylet which has an elongated member having a central portion, a proximal portion and a distal portion wherein said elongated member is contoured from said proximal section to said distal section and wherein said distal portion terminates in a distal tip, a lateral bend formed therein and the distal end of the endotracheal intubation tube includes an opening which is directed through an endotracheal intubation tube having a proximal end, a distal end and a thin wall tube defining a hollowed out central area wherein the distal portion of the intubating stylet is passed through to the proximal end of the endotracheal intubation tube and the lateral bend of the distal tip is passed through said opening;

transporting the central portion of the intubating stylet through the proximal end of the endotracheal intubation tube directing the distal tip of the intubating stylet towards the distal end of the endotracheal intubation tube; and transporting the proximal section of the intubating stylet to a point where the distal section of the intubating stylet is located relative to the distal section of the endotracheal intubation tube.

* * * * *